United States Patent
Zhao et al.

(10) Patent No.: US 8,043,341 B2
(45) Date of Patent: Oct. 25, 2011

(54) SPINAL FIXATION SUPPORT DEVICE AND METHODS OF USING

(75) Inventors: Chunfeng Zhao, Rochester, MN (US); Bradford L. Currier, Rochester, MN (US); Fredrick M. Schultz, Rochester, MN (US); Kai-Nan An, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1209 days.

(21) Appl. No.: 11/301,473

(22) Filed: Dec. 13, 2005

(65) Prior Publication Data

US 2006/0122598 A1  Jun. 8, 2006

Related U.S. Application Data

(63) Continuation of application No. 10/185,322, filed on Jun. 28, 2002, now Pat. No. 7,060,066.

(51) Int. Cl.
*A61B 17/70* (2006.01)

(52) U.S. Cl. .................................................. 606/264

(58) Field of Classification Search ............. 606/246, 606/250, 259, 260, 264, 265, 300, 301, 304, 606/309, 310
See application file for complete search history.

(56) References Cited

U.S. PATENT DOCUMENTS

| | | | |
|---|---|---|---|
| 3,561,437 A | 2/1971 | Orlich | |
| 5,242,444 A | 9/1993 | MacMillan | |
| 5,334,205 A | 8/1994 | Cain | |
| 5,382,248 A | 1/1995 | Jacobson et al. | |
| 5,470,333 A | 11/1995 | Ray | |
| 5,545,164 A | 8/1996 | Howland | |
| 5,562,735 A | 10/1996 | Margulies | |
| 5,772,680 A * | 6/1998 | Kieturakis et al. | 606/190 |
| 5,814,046 A | 9/1998 | Hopf | |
| 6,004,322 A | 12/1999 | Bernstein | |
| 6,083,226 A | 7/2000 | Fiz | |
| 6,179,838 B1 | 1/2001 | Fiz | |
| 6,264,656 B1 | 7/2001 | Michelson | |
| 6,270,484 B1 * | 8/2001 | Yoon | 604/264 |
| 6,296,665 B1 | 10/2001 | Strnad et al. | |
| 6,554,834 B1 | 4/2003 | Crozet et al. | |
| 6,558,386 B1 | 5/2003 | Cragg | |
| 6,565,571 B1 | 5/2003 | Jackowski et al. | |
| 6,620,185 B1 | 9/2003 | Harvie et al. | |
| 6,623,485 B2 | 9/2003 | Doubler et al. | |
| 6,645,207 B2 | 11/2003 | Dixon et al. | |
| 2003/0060823 A1 | 3/2003 | Bryan | |

OTHER PUBLICATIONS

Benzel et al., "Crossed-screw fixation of the unstable thoracic and lumbar spine," *J. Neurosurg.*, 1995, 82:11-16.

Cigliano et al., "A New Instrumentation System for the Reduction and Posterior Stabilization of Unstable Thoracolumbar Fractures," *Neurosurgery*, 1992 30(2):208-217.

(Continued)

*Primary Examiner* — Anu Ramana
(74) *Attorney, Agent, or Firm* — Fish & Richardson P.C.

(57) ABSTRACT

The invention provides for a spinal fixation support device to be used in conjunction with spinal fixation instrumentation. The invention further provides for methods of using the spinal fixation support device. In addition, the invention provides for a spinal fixation system that includes a spinal fixation support device of the invention and can further include spinal fixation instrumentation.

10 Claims, 10 Drawing Sheets

OTHER PUBLICATIONS

Dickman et al., "Transpedicular screw-rod fixation of the lumbar spine: operative technique and outcome in 104 cases," *J. Neurosurg.*, 1992, 77:860-870.

Dooris et al., "Load-Sharing Between Anterior and Posterior Elements in a Lumbar Motion Segment Implanted With an Artificial Disc," *Spine*, 2001, 26(6):E122-E129.

Esses et al., "Complications Associated with the Technique of Pedicle Screw Fixation," *Spine*, 1993, 18(15):2231-2239.

Lim et al., "Biomechanics of Transfixation in Pedicle Screw Instrumentation," *Spine*, 1996, 21(19):2224-2229.

Louis et al., "Posterior Approach With Louis Plates for Fractures of the Thoracolumbar and Lumbar Spine With and Without Neurologic Deficits," *Spine.*, 1998, 23(18):2030-2040.

Matsuzaki et al., "Problems and Solutions of Pedicle Screw Plate Fixation of Lumbar Spine," 1990, 15(11):1159-1165.

* cited by examiner

SPINAL FIXATION SUPPORT DEVICE AND METHODS OF USING

CROSS-REFERENCE TO RELATED APPLICATIONS

This application is a continuation of and claims the benefit of priority under 35 U.S.C. §120 to U.S. application Ser. No. 10/185,322 having a filing date of Jun. 28, 2002 now U.S. Pat. No. 7,060,066. The disclosure of the prior application is incorporated by reference in its entirety.

TECHNICAL FIELD

This invention relates generally to an orthopedic device, and more specifically, to a spinal fixation support device and methods of using such a device.

BACKGROUND

During the last 30 years, the development of instrumentation for internal spinal fixation has evolved rapidly to provide a variety of surgical options. In order to preserve motion segments, avoid long fusion, and provide a stable construct, posterior short-segment pedicle instrumentation (SSPI) has been widely used in unstable vertebral fracture for short segment fixation. Although fusion rates have improved with the use of SSPI, a high rate of instrumentation failure is still a significant problem. In most cases, instrumentation failure occurs due to either implant failure or bone failure. Implant failure occurs when a screw bends or breaks. Bone failure occurs when the bone is weak and/or osteoporotic, resulting in loosening, toggling, or pullout of the screws. In cases of failure, a second operation is necessary, leading to increased risk of complications and higher medical costs. Anterior loading to a posterior construct is a major reason for failure of SSPI. Large axial loading and physiological movement generates significant bending moment to a posterior construct. SSPI combined with anterior fusion has been recommended in order to reduce the anterior-posterior bending moment to posterior constructs. However, a second operation has to be performed from an anterior approach, increasing risk and medical costs.

SUMMARY

The invention provides a spinal fixation support device and methods of using such a device in conjunction with spinal fixation instrumentation. In addition, the invention provides for a spinal fixation system that includes a spinal fixation support device of the invention and spinal fixation instrumentation. The spinal fixation support device reduces the bending moment applied to spinal fixation instrumentation, thus reducing instrumentation failure and increasing the effectiveness of spinal fixation instrumentation.

In one aspect, the invention provides methods for spinal fixation. A method of the invention for spinal fixation includes inserting the distal end of a first pillar into a compromised vertebra, wherein the distal end of the first pillar contacts the lower endplate of a vertebra immediately above the compromised vertebra; inserting the distal end of a second pillar into the compromised vertebra, wherein the distal end of the second pillar contacts the upper endplate of a vertebra immediately below the compromised vertebra; and connecting the proximal ends of the first and second pillars to spinal fixation instrumentation. Such a method also can be used for reducing anterior compression during spinal fixation.

The method can further include the step of placing bone cement at the interface between the distal end of at least one of the first and second pillars and the end plate of the vertebra immediately above or immediately below the compromised vertebra. In one embodiment, cannulated pillars are used and the bone cement is injected through the pillar.

In another aspect, the invention provides spinal fixation systems. Spinal fixation systems of the invention can include spinal fixation instrumentation; at least one pillar having a proximal and a distal end; and at least one connector configured to attach the proximal end of the pillar to the spinal fixation instrumentation. Spinal fixation instrumentation generally includes one or more longitudinal members, one or more pedicle screws, and one or more connectors for attaching longitudinal members to pedicle screws In yet another aspect, the invention provides spinal fixation support devices. Spinal fixation support devices generally include at least one pillar with a proximal and a distal end, and a connector adapted to simultaneously engage and attach the pillar and spinal fixation instrumentation. A spinal fixation support system also is provided by the invention, which includes a spinal fixation support device of the invention and one or more devices for securing the connector to the pillar and to the spinal fixation instrumentation.

In another aspect, the invention provides a pillar for use with spinal fixation instrumentation. A pillar of the invention generally has a substantially rod-like structure, and further has a distal end for engaging a vertebra and a proximal end for engaging spinal fixation instrumentation.

In a further aspect of the invention, and in a spinal fixation system wherein the spinal fixation system comprises spinal fixation instrumentation, wherein the spinal fixation instrumentation comprises one or more longitudinal members, one or more pedicle screws, and one or more connectors for attaching longitudinal members to pedicle screws, the inventive improvement includes at least one pillar with a proximal and a distal end; and at least one connector to attach the proximal end of the pillar to the spinal fixation instrumentation.

In one embodiment, the spinal fixation instrumentation is posterior short-segment pedicle instrumentation. In addition, the distal end of the pillars can include one or more anchoring members for engaging the endplate of the vertebra immediately above or immediately below the compromised vertebra. Such anchoring members can be teeth-like members. The distal ends of the pillars can form an oblique plane relative to the longitudinal axis of the pillars, while the proximal end of each pillar can be adapted to engage the spinal fixation instrumentation. For example, the proximal end can have threads. Further, either or both pillars can be cannulated.

The location of insertion of the first pillar can be determined by the intersection of a vertical line at the lateral border of the superior articular process of the compromised vertebra and a horizontal line at the lower margin of the transverse process of the compromised vertebra. Likewise, the location of insertion of the second pillar can be determined by the intersection of a vertical line at the lateral border of the superior articular process of the compromised vertebra and a horizontal line at the upper margin of the transverse process of the compromised vertebra. In addition, the first pillar and second pillar are generally advanced at about a 45° angle with respect to the transverse plane of the compromised vertebra.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DESCRIPTION OF DRAWINGS

Like reference symbols in the various drawings indicate like elements.

DETAILED DESCRIPTION

Transpedicular fixation has become an important method for posterior spinal fixation. Spinal fixation can be necessary when one or more vertebrae have been compromised due to, for example, an unstable spine fracture or a burst fracture. Spinal fixation instrumentation is particularly well suited for fixation in the lumbar and thoracic region, and can assist in the load-bearing ability of the spine that is lost due to disease or injury of one or more vertebrae while still preserving motion in the adjacent normal segments. Pedicle screw instrumentation, however, is susceptible to failure because of heavy loads and repetitive stresses placed upon the instrumentation. Instrumentation failure typically results in additional surgeries, including surgical intervention from either or both an anterior or posterior approach. Multiple surgeries, particularly those that access the spine both anteriorly and posteriorly, significantly increase both the costs and the risks to the patient.

The invention provides for a spinal fixation support device to be used with posterior spinal fixation instrumentation to improve the treatment of spinal injuries and diseases and to reduce the frequency of instrumentation failure. A spinal fixation support device of the invention acts by reducing the bending moment applied to spinal fixation instrumentation. Spinal fixation support devices of the invention significantly improve the load-bearing capacity of spinal fixation instrumentation and do not increase the number of motion segments affected. A spinal fixation support device of the invention can be used in conjunction with spinal fixation instrumentation to treat traumatic fractures, pathological fractures (due to, e.g., osteoporosis, or tumor infiltration), or fractures resulting from metastatic disease. Advantageously, a spinal fixation support device of the invention does not require a second surgery to install, and can obviate the need for anterior fusion, thereby reducing costs and risk to the patient. The invention further provides for methods of using a spinal fixation support device. In addition, the invention provides for spinal fixation systems that include a spinal fixation support device of the invention and spinal fixation instrumentation.

Figure 1:
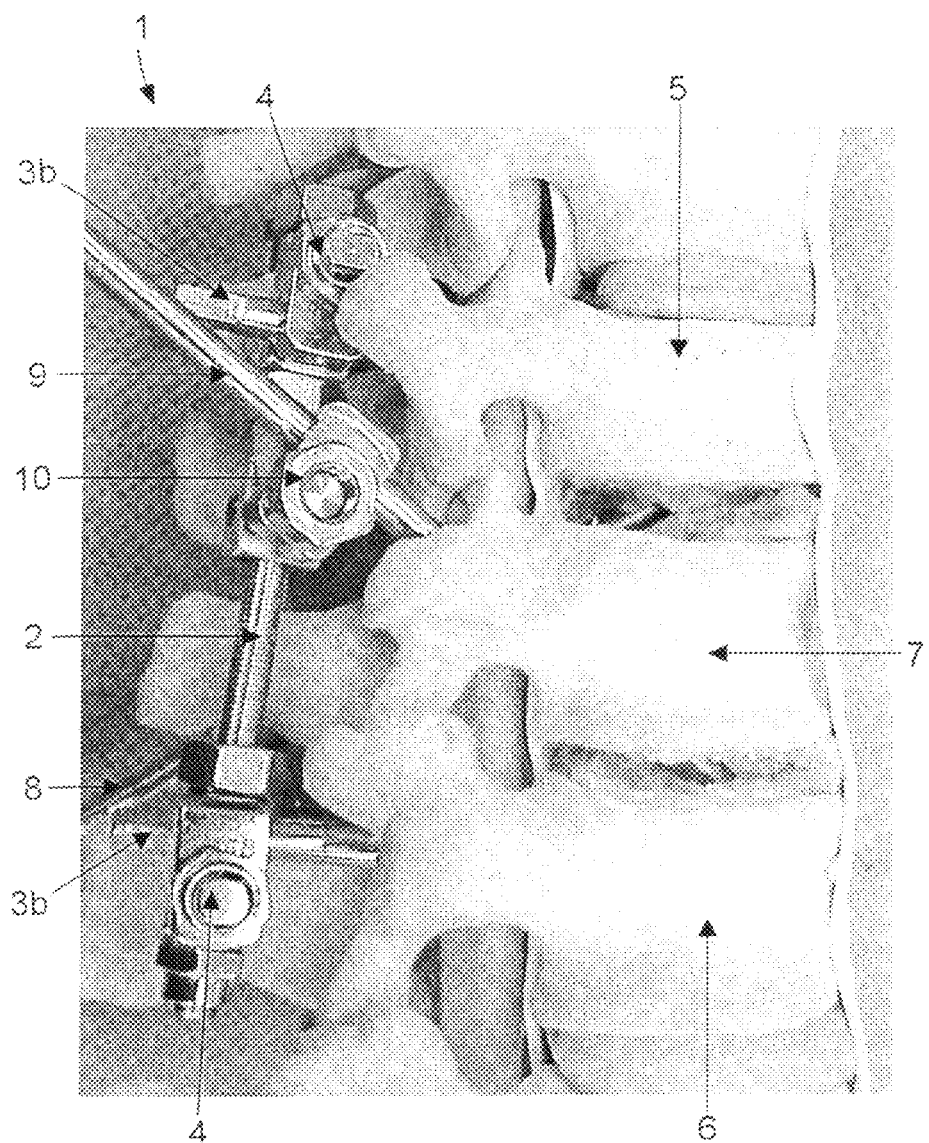
FIG. 1 shows a section of synthetic spine in which Dick's spinal fixation instrumentation and a spinal fixation support device of the invention has been installed.

FIG. 1 shows a spinal fixation system (1) of the invention. Spinal fixation instrumentation as used herein minimally includes one or more longitudinal members (2), and pedicle screws (3) for anchoring the longitudinal members to healthy vertebrae (5,6) above (5) and below (6) a compromised vertebra (7). Longitudinal members (2) are attached to the superior (3a) and inferior (3b) pedicle screws via longitudinal member-pedicle screw connectors (4). A spinal fixation support device of the invention includes pillars (8, 9) that can be attached to the longitudinal members (2) of the spinal fixation instrumentation via connectors (10).

Because the pedicle offers a strong point of attachment to the spine, transpedicular spinal fixation instrumentation has been developed to provide support across the compromised segment and, to a certain degree, immobilize the segment. As used herein, "compromised vertebra" or "compromised segment" refers to a vertebra or segment of vertebrae in which the load-bearing ability has been reduced due to, for example, damage, disease, or injury. The thoracic, lumbar, and sacral vertebrae are suitable for receiving transpedicular spinal fixation instrumentation. The pedicles of the thoracic, lumbar, and sacral vertebrae are oval-shaped and composed of a thick collar of cortical bone surrounding a core of cancellous bond. The narrowest portion of the pedicle is the transverse width, which usually determines the size of pedicle screw used. Typically, the major screw diameter is 70-80% of the pedicle diameter. The flex, rigidity, and bending strength of pedicle screws are determined by the minor screw diameter. Generally, pedicle screws are long enough to penetrate 70-80% of the depth of the vertebral body.

The longitudinal member (2) in the spinal fixation system shown in FIG. 1 is a rod. Plates, however, also are used in spinal fixation instrumentation and are suitable for use with a spinal fixation support device of the invention (see, for example, FIG. 2). The length of the longitudinal member will be dependent upon the distance between the healthy vertebrae above and below the compromised vertebra. Spinal fixation instrumentation, including the longitudinal members (2), the pedicle screws (3), and the longitudinal member-pedicle screw connectors (4) are generally constructed using titanium, titanium-alloy, or stainless steel materials.

In one embodiment, posterior short-segment pedicle instrumentation (SSPI) is used. Examples of SSPI include Dick's instrumentation (e.g., Internal Skeleton Fixation System (ISFS), Sulzer Ltd., Winterthur, Switzerland), which utilizes rods as longitudinal members, and Louis instrumentation (e.g., Louis et al., 1998, *Spine*, 23:2030-40), which utilizes plates as longitudinal members. It is intended that spinal fixation support devices of the invention (i.e., pillars and connectors) be adapted for use with any type of posterior transpedicular spinal fixation instrumentation.

Figure 3:
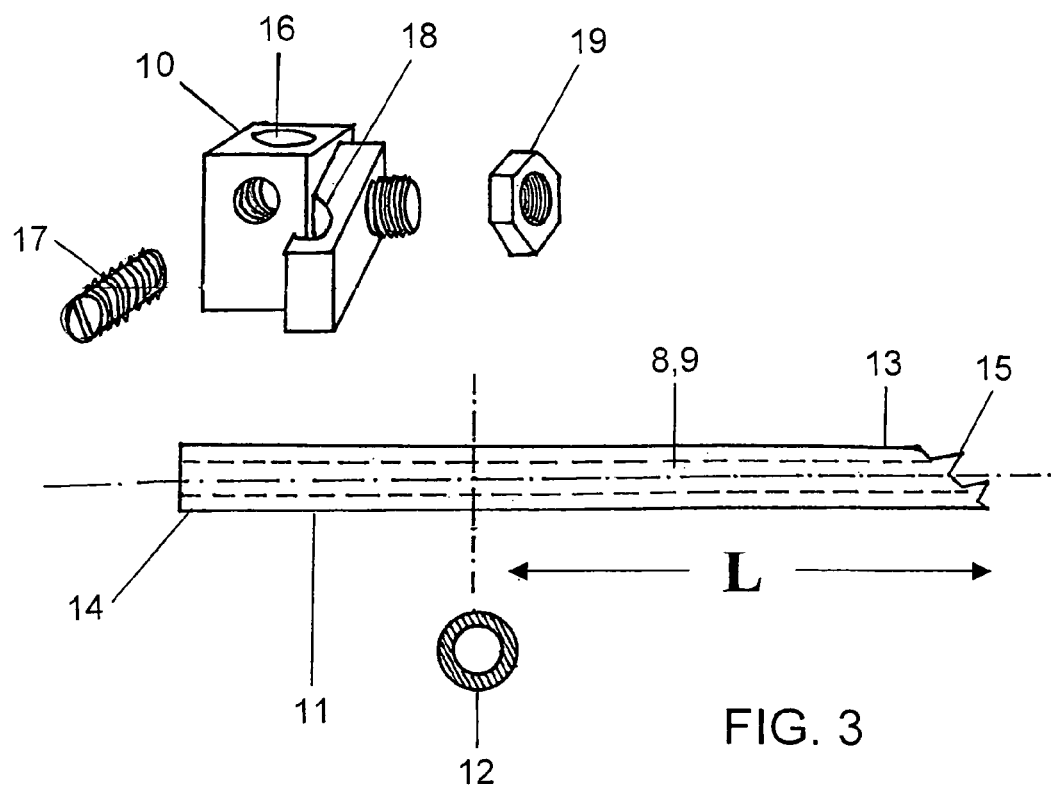
FIG. 3 is a schematic showing an embodiment of a pillar and a connector for attaching a pillar to spinal fixation instrumentation.

As shown in FIG. 1, a spinal fixation support device of the invention to be used with spinal fixation instrumentation generally includes a superior (8) and an inferior (9) pillar, and connectors (10) for attaching such pillars to the longitudinal members (2) of the spinal fixation instrumentation. The orientation of the superior pillar (8) is caudaly posterior to cephalaly anterior. The superior pillar (8) penetrates the upper endplate of the compromised vertebral body. FIG. 3 shows a side-view (11) and a cross-sectional view (12) of a pillar (8,9) for use in a spinal fixation support device of the invention. The distal end of the pillar (13) shown in FIG. 3 forms an oblique plane relative to the longitudinal axis (L) of the pillar. The distal end of a pillar (13) also can have one or more anchoring members (15) for engaging the endplate of a healthy vertebra (5,6). The anchoring members (15) can be, for example, teeth-like members. Teeth-like members as shown in FIG. 3 for example, can be forcibly impacted to engage the endplate of a healthy vertebra above or below the compromised vertebra. The proximal end of a pillar (14) can be adapted to engage a connector (10) such that the pillar can be attached to spinal fixation instrumentation. For example, the proximal end of a pillar (14) can be attached to spinal fixation instrumentation via a connector (10).

Figure 2A:
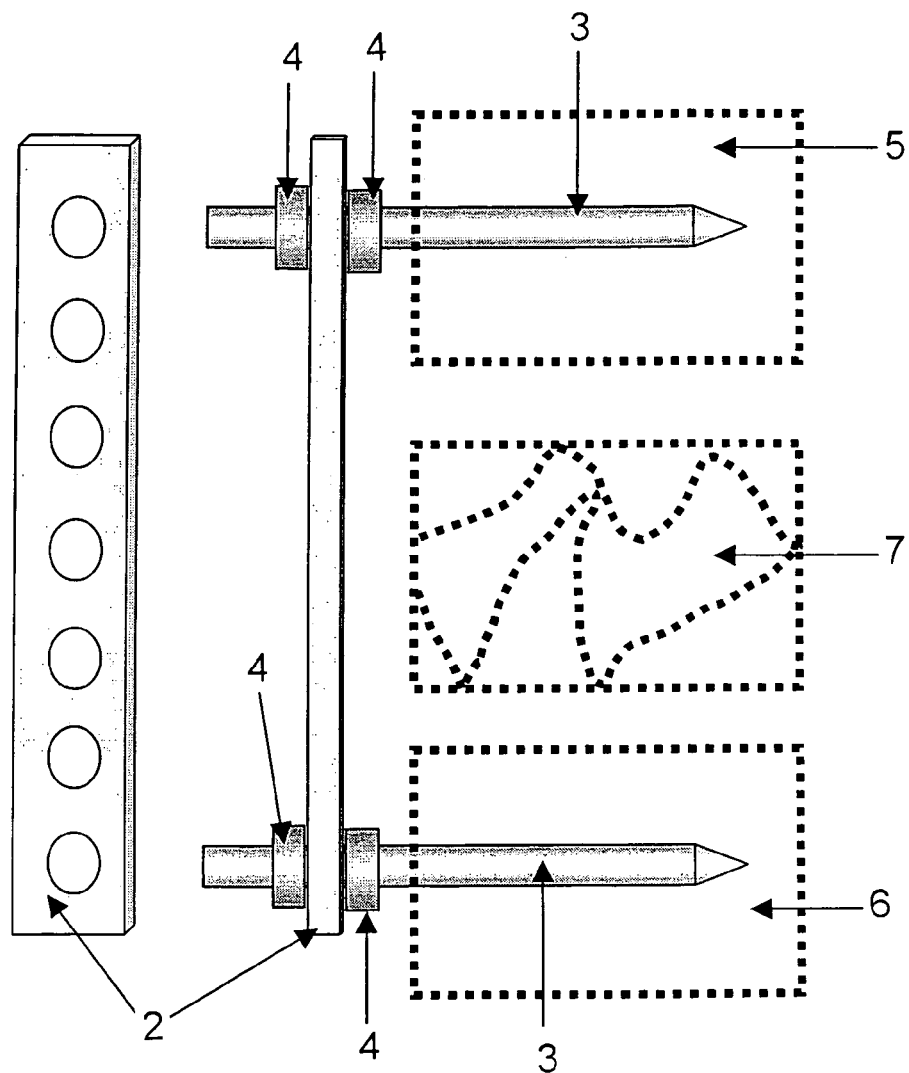
FIG. 2 is a schematic drawing of the components of Louis spinal fixation instrumentation (FIG. 2A) and of Louis spinal fixation instrumentation with a spinal fixation support device of the invention (FIG. 2B).
Figure 2B:
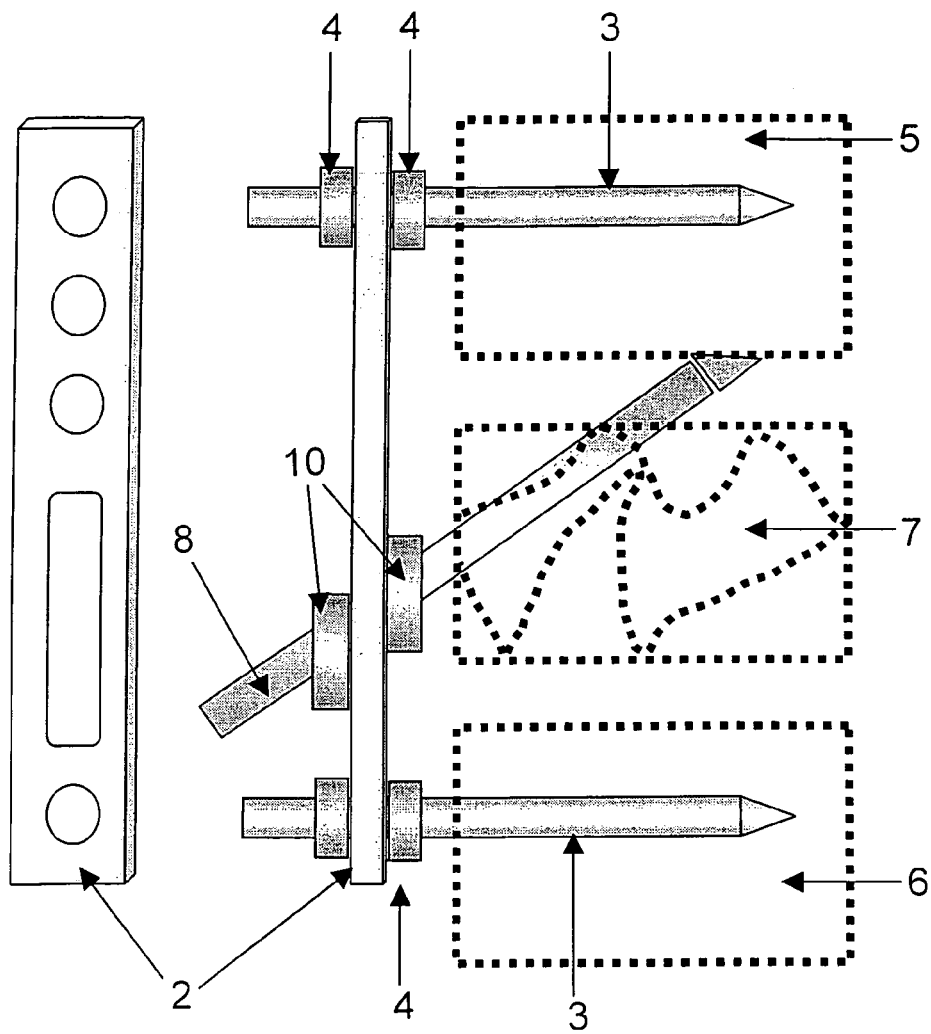

As noted above, the pillar system of the invention may be adapted for use with any type of posterior spinal fixation instrumentation. Certain embodiments of the invention discussed herein are described in reference to Dick's instrumentation. Another example of posterior pedicle screw instrumentation suitable for use with the pillar system of the invention, as mentioned above, is Louis instrumentation. FIG. 2A illustrates conventional Louis instrumentation; FIG. 2B illustrates how Louis instrumentation can be modified to be used with a spinal fixation support device of the invention. For example, each plate can be modified by making a slot or an oblique hole for insertion and fixation of the pillar. A pillar (8) then can be fixed to a longitudinal member (2) with connectors (10).

Pillars of the invention can be constructed in a variety of different lengths, or can be constructed in a single length that is then sized and/or positioned appropriately once the patient's spine has been exposed and/or the spinal fixation instrumentation has been fitted. Pillars can have a diameter of from about 5 millimeters (mm) up to about one-quarter of an inch. Like other spinal instrumentation, pillars for use in a spinal fixation support device of the invention can be fabricated out of titanium, or stainless steel. In addition, pillars of the invention can be cannulated.

Connectors (10) to be used in a spinal fixation support device of the invention are designed to appropriately engage both a proximal end of a pillar (14) and a longitudinal member (2) of spinal fixation instrumentation. A connector of the invention used to attach a pillar to a longitudinal member can be a fixed angle connector or a variable angle connector. The embodiment in FIG. 2B shows the pillar (8) attached to the longitudinal Member (2) by two threaded nut connectors (10). As the embodiment shown in FIG. 3 demonstrates, a connector suitable for use in the invention can have a hole (16) for receiving the longitudinal member (2). The longitudinal member (2) can be secured to the connector (10) by a screw (17). The proximal end of a pillar (14) can be positioned in a receiving groove (18) of the connector (10), and the pillar can then be secured to the connector (10) by a nut (19). In another embodiment, the connector (10) for attaching a pillar (8,9) to a longitudinal member (2) can be similar or identical to a connector (4) used to attach a longitudinal member (2) to a pedicle screw (3). Connectors (10) suitable for use in the invention can be made with titanium, titanium-alloys, or stainless steel. The mechanics of connectors, including threaded fasteners, are known in the art. A connector (10) adapted to engage both a longitudinal member of spinal fixation instrumentation and the proximal end of a pillar (14) should be designed to optimize load carrying capacity while reducing load stress.

The invention further provides for methods of spinal fixation using the spinal fixation support device of the invention in conjunction with spinal fixation instrumentation. Spinal fixation is preferably performed on a minimal number of vertebrae (e.g., from the first vertebra cephalad to the compromised vertebra to the first vertebra caudal to the compromised vertebra). Installation of spinal fixation instrumentation is well known and routine in the art. For surgical procedures involving installation of spinal fixation instrumentation, patients are placed in the prone position on the operating table. The spine is exposed at the segment(s) to be instrumented and, if necessary, decompressed. The pedicles are identified, and a hole is made using, for example, a drill or a Steinmann pin. Pedicle screw size is usually preselected based on the characteristics of the particular vertebrae determined by, for example, CT scan, or MRI. The pedicle screws are placed into the prepared holes and advanced appropriately. Pedicle identification, hole preparation, and screw placement are generally preformed under fluoroscopic observation (e.g., intraoperative anteroposterior, oblique, and lateral fluoroscopy). If fusion is being performed, the fusion site is prepared by decorticating the bone fusion surfaces (e.g., the transverse processes, and the facet joints) with a high-speed drill. After bone grafts (e.g., using autogenous iliac bone) are positioned, the longitudinal member is attached to the pedicle screws.

Problematically, axial loading and physiological movement inherently generates bending moment, which results in stress on the spinal fixation instrumentation. Due to lumbar lordosis, the screws are subjected to large cantilever bending forces that can cause the screws to break or bend. Failure of spinal fixation instrumentation is particularly prevalent noticeable at the thoracolumbar junction because compressive forces act more anteriorly in this region due to the physiologic kyphosis. Particularly in types of spinal fixation instrumentation that utilize a rod for the longitudinal member, it is common in the art to use one or more transfixator members that crosslink the longitudinal rods and improve the stability of the instrumentation (see, for example, Lim et al., 1996, *Spine*, 21:2224-9). Transfixation of the longitudinal rods provides an additional stabilizing effect to spinal fixation instrumentation during axial rotation, but does not stabilize the instrumentation with respect to flexion, extension, and lateral bending moments.

Figure 4A:
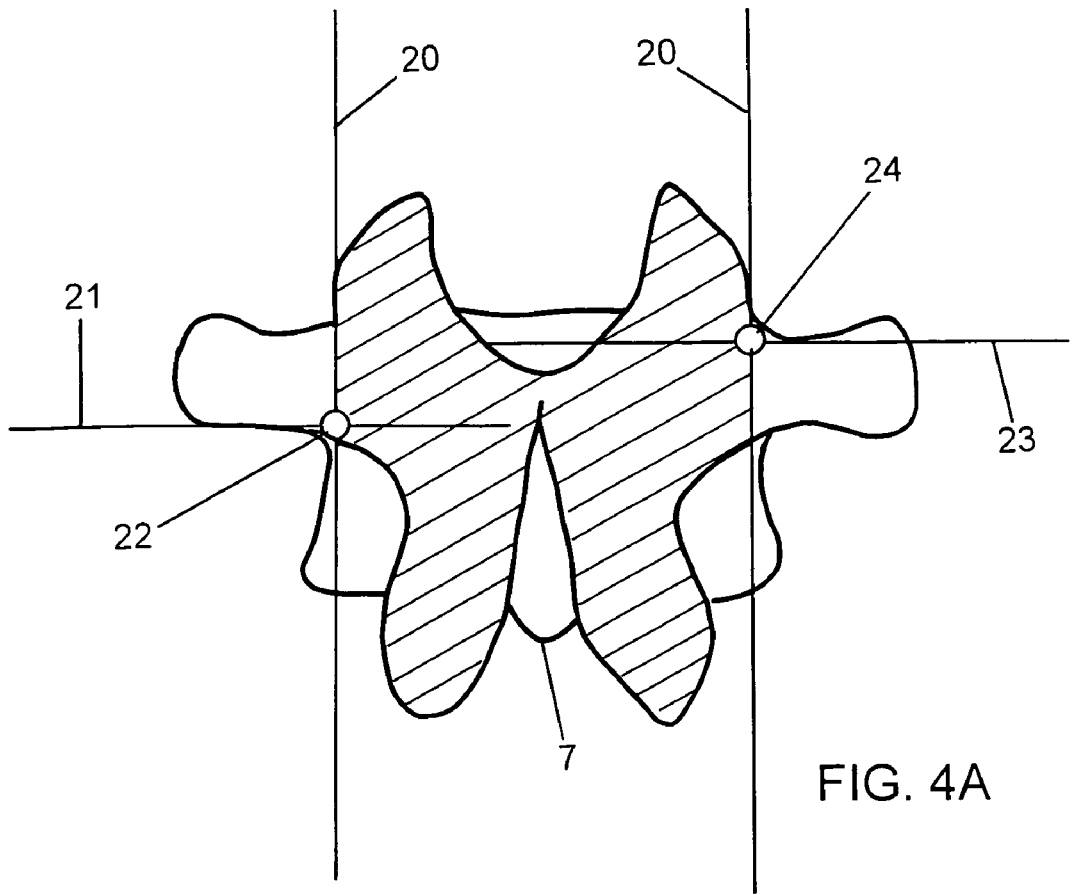
FIG. 4A is a schematic showing the reference lines that can be used to introduce and position spinal fixation support pillars of the invention.
Figure 4B:
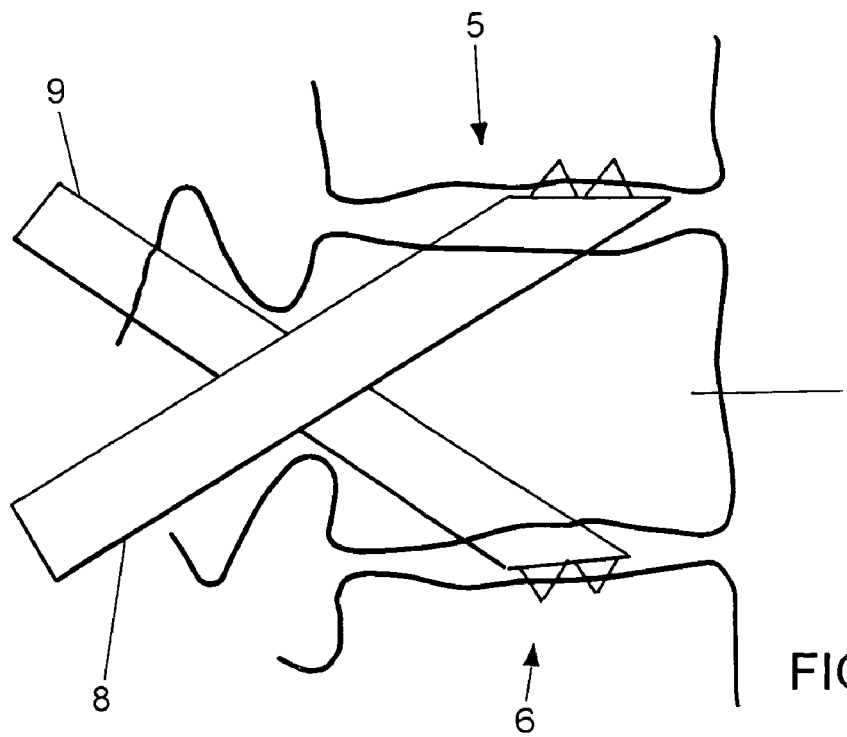
FIG. 4B is a cross-sectional view of a spine after placement of spinal fixation support pillars of the invention.

It is intended that the pillars of the spinal fixation support device of the invention carry a portion of the axial load placed upon spinal fixation instrumentation. Therefore, pillars of the invention can reduce the bending moment placed on the instrumentation. As such, the load on the pedicle screw is reduced, which reduces the failure rate of the spinal fixation instrumentation. FIG. 4 illustrates how the point of entry of each pillar is determined (FIG. 4A) and shows a cross-sectional view of the installed pillars (FIG. 4B). The intersection

(22) of a vertical line at the lateral border of the superior articular process (20) of the compromised vertebra and a horizontal line at the low margin of the transverse process (21) of the compromised vertebra determines the point of entry of a superior pillar (8). The point of entry of an inferior pillar (9) is determined by the intersection (24) of the vertical line at the lateral border of the superior articular process (20) of the compromised vertebra and a line delineating the upper margin of the transverse process (23) of the compromised vertebra.

When installing the spinal fixation support device, the path of pillar insertion generally passes obliquely through a pedicle and a vertebral body of a compromised vertebra from a posterior approach (either superiorly and inferiorly), and then crosses the endplate of that vertebra and reaches the endplate of an adjacent healthy vertebra. The superior pillar is oriented from caudally posterior to cephalaly anterior. The distal end of the superior pillar is positioned such that the oblique plane is flush with the lower endplate of the healthy vertebra immediately above the compromised vertebra. The inferior pillar is oriented from cephalaly posterior to caudally anterior. The distal end of the inferior pillar is positioned such that the oblique plant is flush with the upper endplate of the vertebra immediately below the compromised vertebra. The pillars are advanced from the entrance points described above at approximately a 45° angle to the transverse plane of the compromised vertebra until the oblique distal end of each pillar touches the endplate of the appropriate healthy vertebra immediately above or below the compromised vertebra.

Similar to the insertion of pedicle screws, a receiving channel is usually drilled prior to insertion of the pillars. In order to prevent unwanted penetration of the pillar into the endplate of an adjacent vertebra, especially in osteoporotic cases, bone cement can be injected into the interface between the end of the pillar tip and the endplate of the adjacent vertebra. In a cannulated pillar, bone cement can be injected through the lumen of the pillar from the proximal end. The spinal fixation support device is preferably installed simultaneously with the installation of spinal fixation instrumentation, but can be installed subsequent to spinal fixation instrumentation having been installed.

Systems for spinal fixation using a spinal fixation support device of the invention are provided by the invention. Spinal fixation systems provided by the invention can include one or a few pillars suitable for use in an individual, or can include numerous pillars that, for example, encompass a range of different lengths and/or diameters. Spinal fixation systems provided by the invention can likewise include one or more connectors for engaging a variety of longitudinal members, or can include connectors suitable for attaching a pillar specifically to a rod longitudinal member or specifically to a plate longitudinal member. A spinal fixation system of the invention can, but does not necessarily, include spinal fixation instrumentation (e.g., one or more longitudinal members, one or more pedicle screws, and one or more longitudinal member-pedicle screw connectors). A spinal fixation instrumentation support system is also provided by the invention. In addition to one or more pillars and one or more connectors, a spinal fixation support system of the invention can further include a device for securing a pillar to a longitudinal member of spinal fixation instrumentation via a connector. A device for securely attaching the pillar to the longitudinal member can include, for example, a tool (e.g., a wrench). Such a tool (e.g., a torque wrench) can be used to apply a particular or predefined amount of force to the connector to thereby ensure an appropriate load carrying capacity on the pillar and the connector without undue stress on the instrumentation.

The invention will be further described in the following examples, which do not limit the scope of the invention described in the claims.

EXAMPLES

Example 1

Mechanical Testing of the Pillar System Using a Synthetic Resin Spine

Figure 5:
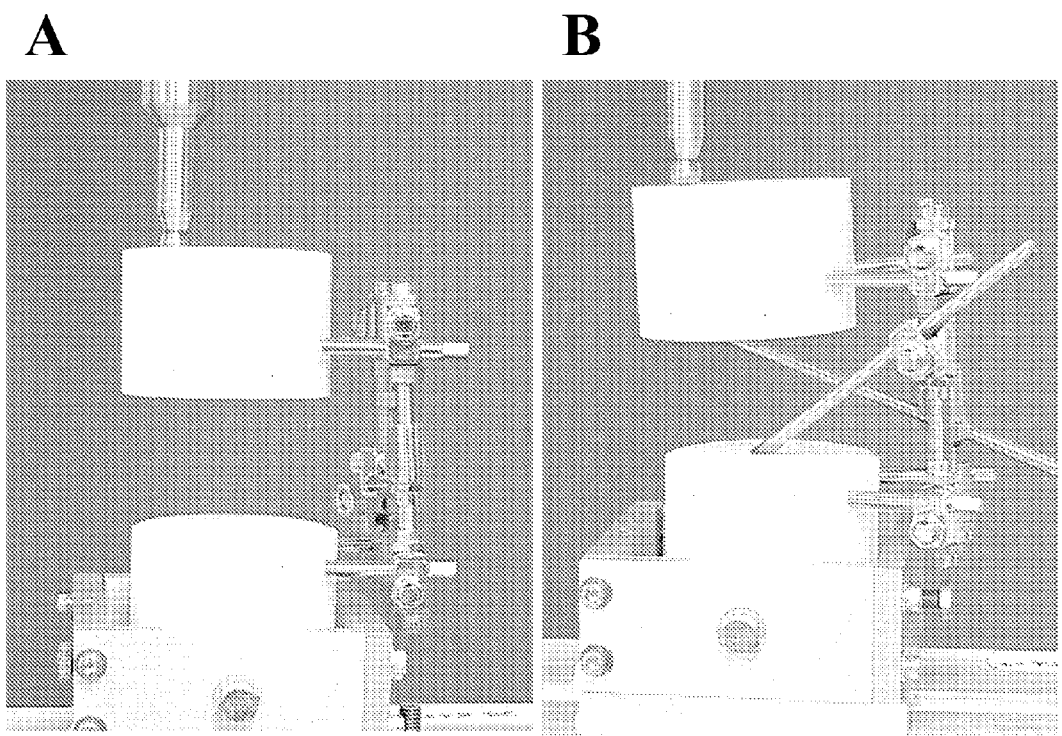
FIG. 5 is a photograph showing a synthetic resin spine used to model forces applied to spinal fixation instrumentation with (FIG. 5B) and without (FIG. 5A) a spinal fixation support device of the invention.
Figure 6:
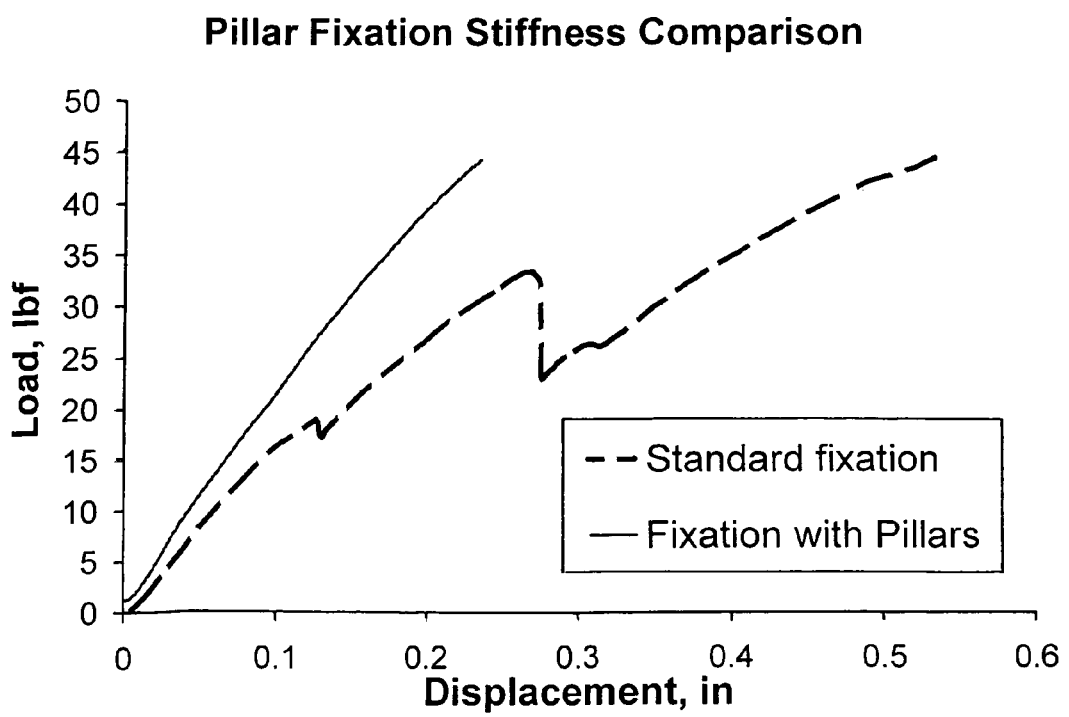
FIG. 6 is a graph showing a comparison of the stiffness of spinal fixation instrumentation used on a synthetic resin spine with and without a spinal fixation support device of the invention.

Mechanical testing of the pillar system was performed using synthetic resin vertebrae (Acetal; Delrin, Precision Punch & Plastics Co., Minnetonka, Minn.). Dick short-segment pedicle instrumentation (Internal skeleton fixation system ISFS; Sulzer Ltd CH-8401, Winterthur, Switzerland) was used as the spinal fixation instrumentation. The specimen was mounted on a servohydraulic machine (MTS, Minneapolis, Minn.). An axial load of 10 N/m torque was applied to the top of the vertebral body (195 Newton load with a 0.052 meter moment arm) (FIG. 5). This axial load to the vertebral body is commonly used for mechanical testing (see, for example, Dooris et al., 2001, *Spine*, 26:E122-9, and references therein). The testing was first performed without a pillar system. After pillars were installed, the test was repeated. The load and displacement of the vertebrae were recorded at 20 Hz. FIG. 6 shows the results from such experiments, and indicates that the stiffness of the pillar system was 2.7-fold higher than that of the standard Dick system without pillar system.

Example 2

Mechanical Testing of the Pillar System Using a Human Cadaver Spine

A human cadaver spine from T12 to L2 was harvested for the mechanical test. The anterior three-fourths of the L1 vertebral body was resected to simulate a severe non-load-bearing situation. Compression of the harvested spine was performed by hand until the T12 touched the L2 anteriorly to create an unstable spine model.

Figure 7B:
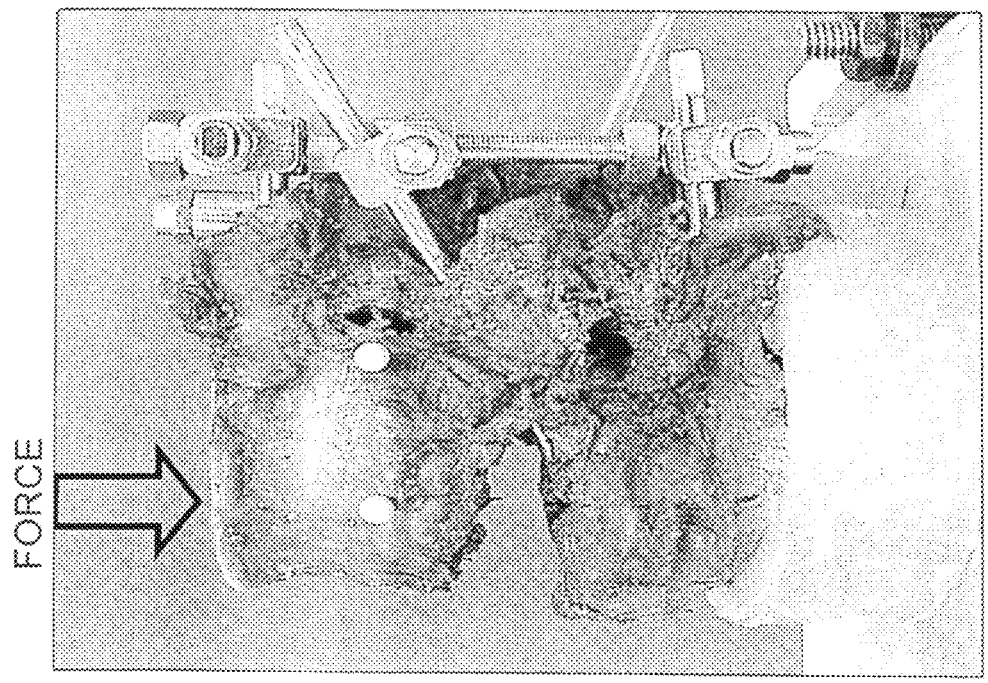
FIG. 7 is a photograph showing a cadaver spine used to model forces applied to spinal fixation instrumentation with (FIG. 7B) and without (FIG. 7A) a spinal fixation support device of the invention.
FIG. 7C shows an X-ray used to confirm positioning of the pedicle screws and pillars.
Figure 7A:
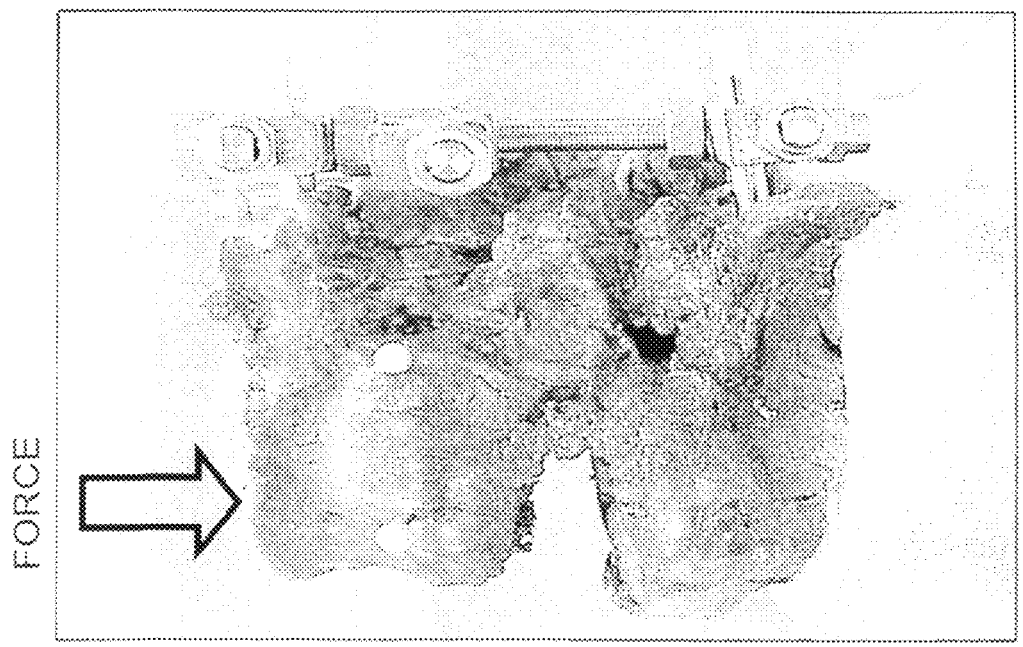

The two pedicles in the L1-fractured vertebra were prepared for pillar insertion as described herein. Following preparation of the holes for pillar insertion, Dick spinal fixation instrumentation using 5 mm pedicle screws was installed between T12 and L1 using a standard surgical procedure as would be performed by an orthopedic surgeon. The bottom of the L2 vertebral body was embedded in bone cement and the specimen was mounted in the servohydraulic machine for mechanical testing (FIG. 7A). An axial load of 7.5, 10, or 15 N/m torque was applied anteriorly to the top of the vertebral body. Mechanical testing was first performed on the spine in which only Dick spinal fixation instrumentation was installed (i.e., without the pillars).

Figure 7C:
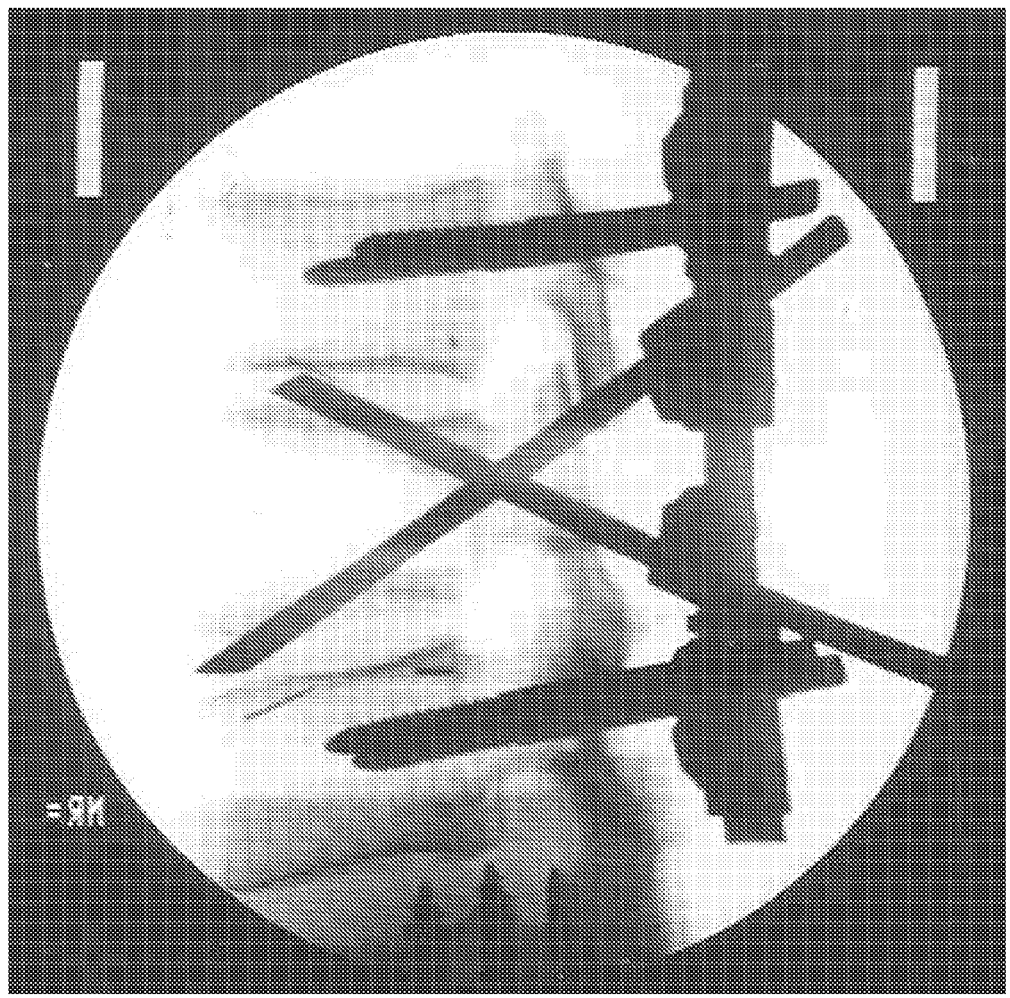
Figure 8:
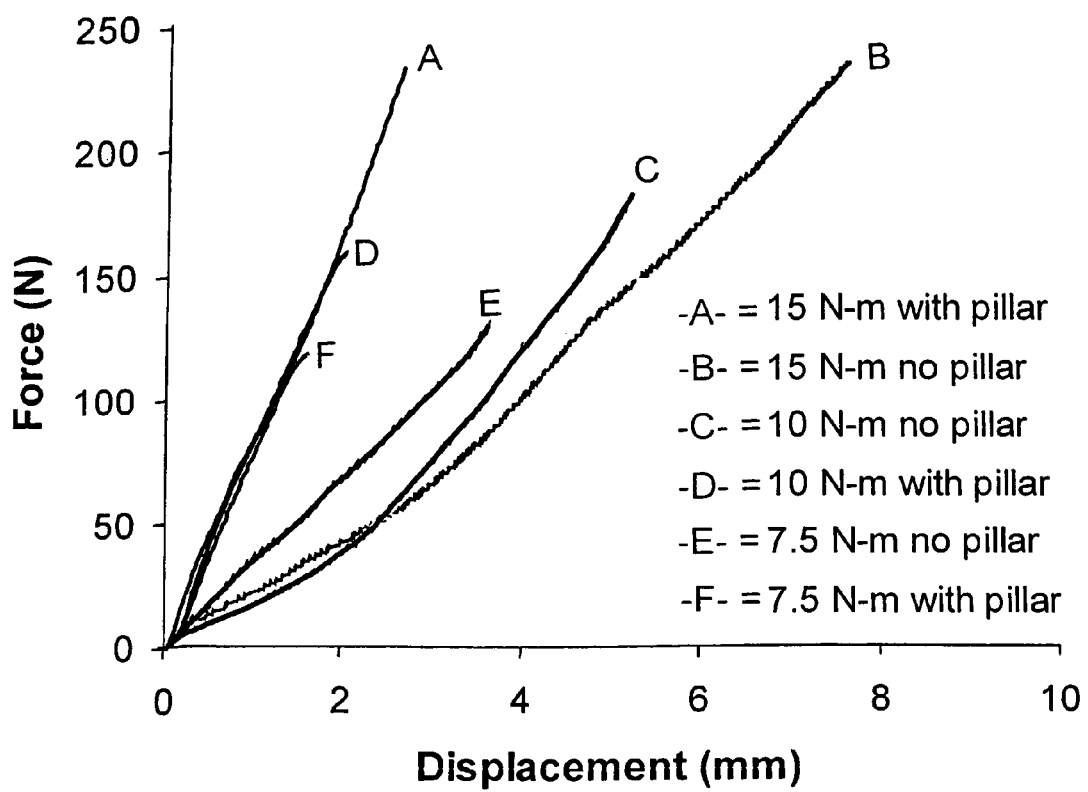
FIG. 8 is a graph showing a comparison of the stiffness of spinal fixation instrumentation on a cadaver spine with and without a spinal fixation support device of the invention.

Following mechanical testing with the spinal fixation instrumentation alone, the pillars were installed. The pillars were advanced through the L1 pedicle holes until the tip of each pillar touched the endplate of the vertebrae immediately above or below L1 (i.e., T12 and L2). The pillars were attached to the Dick instrumentation using a connector as shown in FIG. 3. The spine section was placed in the servohydraulic machine so that the position of the spine and the position of the moment arm did not change (FIG. 7B). An X-ray was taken to confirm that the pedicle screws and pillars were inserted properly within the pedicle (FIG. 7C). The mechanical testing was then performed on the instrumented spine segments in the presence of the pillars. The experiments demonstrated that the strength and stiffness of the Dick instrumentation increased 3-fold after the pillar system was installed (FIG. 8).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A spinal fixation system comprising:
spinal fixation instrumentation comprising one or more longitudinal members, one or more pedicle screws, and one or more first connectors for attaching longitudinal members to pedicle screws;
at least one pillar having a proximal and a distal end, wherein said distal end terminates at a surface that forms an oblique plane relative to the longitudinal axis of said pillar, wherein said oblique plane surface at said distal end comprises one or more anchoring members to engage an endplate of a vertebra, wherein said anchoring members protrude from said oblique plane surface, wherein said proximal end is adapted to engage a connector; and
at least one second connector configured to attach the proximal end of said pillar to said spinal fixation instrumentation,
wherein said pillar is configured to be inserted through a compromised vertebra such that said proximal end is connected to said spinal fixation instrumentation and said oblique plane surface at said distal end is flush with the endplate of a vertebra immediately above or below said compromised vertebra, wherein said anchoring members are configured to be impacted into said endplate so as to secure said pillar, wherein installation of said at least one pillar in conjunction with said spinal fixation instrumentation serves to reduce the axial load placed on said spinal fixation instrumentation.

2. The system of claim 1, wherein said spinal fixation instrumentation is posterior short-segment pedicle instrumentation.

3. The system of claim 1, wherein said one or more anchoring members are teeth-like members.

4. The system of claim 1, wherein the proximal portion of said pillar is adapted to engage said spinal fixation instrumentation.

5. The system of claim 1, wherein said pillar is cannulated.

6. In a spinal fixation system wherein the spinal fixation system comprises spinal fixation instrumentation, wherein said spinal fixation instrumentation comprises one or more longitudinal members, one or more pedicle screws, and one or more first connectors for attaching said longitudinal members to said pedicle screws, the improvement comprises:
at least one pillar with a proximal and a distal end, wherein said distal end terminates at a surface that forms an oblique plane relative to the longitudinal axis of said pillar, wherein said oblique plane surface at said distal end comprises one or more anchoring members to engage an endplate of a vertebra, wherein said anchoring members protrude from said oblique plane surface, wherein said proximal end is adapted to engage a connector; and
at least one second connector to attach the proximal end of said pillar to said spinal fixation instrumentation,
wherein said pillar is configured to be inserted through a compromised vertebra such that said proximal end is connected to said spinal fixation instrumentation and said oblique plane surface at said distal end is flush with the endplate of a vertebra immediately above or below said compromised vertebra, wherein said anchoring members are configured to be impacted into said endplate so as to secure said pillar, wherein installation of said at least one pillar in conjunction with said spinal fixation instrumentation serves to reduce the axial load placed on said spinal fixation instrumentation.

7. The system of claim 6, wherein said spinal fixation instrumentation is posterior short-segment pedicle instrumentation.

8. The system of claim 6, wherein said one or more anchoring members are teeth-like members.

9. The system of claim 6, wherein the proximal portion of said pillar is adapted to engage said spinal fixation instrumentation.

10. The system of claim 6, wherein said pillar is cannulated.

* * * * *